(12) United States Patent
Ren et al.

(10) Patent No.: US 8,481,511 B2
(45) Date of Patent: *Jul. 9, 2013

(54) PHARMACEUTICAL COMPOSITION CONTAINING DOCETAXEL-CYCLODEXTRIN INCLUSION COMPLEX AND ITS PREPARING PROCESS

(75) Inventors: Yong Ren, Jiangsu (CN); Jianfeng Gao, Jiangsu (CN); Shuqin Yu, Jiangsu (CN); Ling Wu, Jiangsu (CN)

(73) Assignee: Hainan Hdeton Science and Technology Co., Ltd. (CN)

( * ) Notice: Subject to any disclaimer, the term of this patent is extended or adjusted under 35 U.S.C. 154(b) by 354 days.

This patent is subject to a terminal disclaimer.

(21) Appl. No.: 12/440,942

(22) PCT Filed: Oct. 13, 2006

(86) PCT No.: PCT/CN2006/002692
§ 371 (c)(1),
(2), (4) Date: Mar. 12, 2009

(87) PCT Pub. No.: WO2008/031285
PCT Pub. Date: Mar. 20, 2008

(65) Prior Publication Data
US 2010/0048685 A1 Feb. 25, 2010

(30) Foreign Application Priority Data
Sep. 12, 2006 (CN) .......................... 2006 1 0041531

(51) Int. Cl.
*C08B 37/16* (2006.01)
*A61K 31/715* (2006.01)

(52) U.S. Cl.
USPC ............................................ 514/58; 514/449

(58) Field of Classification Search
None
See application file for complete search history.

(56) References Cited

U.S. PATENT DOCUMENTS

| | | | |
|---|---|---|---|
| 5,684,169 A | 11/1997 | Hamada et al. | |
| 5,804,568 A | 9/1998 | Rubinfeld | |
| 6,218,374 B1 | 4/2001 | Rubinfeld | |
| 6,284,746 B1 | 9/2001 | Szente et al. | |
| 2004/0053888 A1 | 3/2004 | Suzuki et al. | |
| 2005/0009783 A1 | 1/2005 | Kagkadis | |
| 2007/0087999 A1 | 4/2007 | Geczy | |
| 2009/0012042 A1 | 1/2009 | Ren et al. | |
| 2010/0048685 A1 | 2/2010 | Ren et al. | |
| 2011/0015145 A1* | 1/2011 | Bodor ............................ | 514/46 |

FOREIGN PATENT DOCUMENTS

| | | |
|---|---|---|
| CA | 2092979 | 3/1993 |
| CA | 2123946 | 5/1994 |
| CN | 1222321 | 7/1999 |
| CN | 1424112 | 6/2003 |
| CN | 1440748 | 9/2003 |
| CN | 200510095176 | * 11/2005 |
| EP | 1950227 A1 * | 7/2008 |
| WO | 9924073 | 5/1999 |
| WO | WO 9924073 A1 * | 5/1999 |
| WO | 03043602 | 5/2003 |

OTHER PUBLICATIONS

U.S. Appl. No. 12/440,792, filed Mar. 2009, Ren et al.*
Guchelaar et al.; Clinical, Toxicological and Pharmaceutical Aspects of the Antineoplastic Drug Taxol: A Review; Clinical Oncology 1994, pp. 41-48.
Cserhati et al.; Interaction of Taxol and Other Anticancer Drugs With Hydroxypropyl-B-Cyclodextrin; International Journal of Pharmaceutics 1994; pp. 70-75.
Yue et al.; Inclusion Complex of Paclitaxel in Hydroxypropyl-B-Cyclodextrin; Chem. Res. Chinese U. 2005; pp. 750-752.
Dordunoo et al.; Solubility and Stability of Taxol: Effects of Buffers and Cyclodextrins; International Journal of Pharmaceutics 1996; pp. 192-201.
Sharma et al.; Pharmaceutical and Physical Properties of Paclitaxel (Taxol) Complexes With Cyclodextrins; Journal of Pharmaceutical Sciences, vol. 84, No. 10, Oct. 1995; pp. 1223-1230.
Moser et al.; Taxol Inclusion Complexes With a Cyclodextrin Dimer: Possibilities to Detoxify Chemotherapeutics and to Target Drugs Specifically to Tumors?; Journal of Inclusion Phenomena and Macrocyclic Chemistry 2001; pp. 13-18.
Alcaro et al.; Preparation, Characterization, Molecular Modeling and in Vitro Activity of Paclitaxel-Cyclodextrin Complexes; Bioorganic & Medicinal Chemistry Letters 2002; pp. 1637-1641.
U.S. Appl. No. 12/440,792, filed Mar. 11, 2009.
Office Action (Mail Date Apr. 18, 2011) for U.S. Appl. No. 12/440,792, filed Mar. 11, 2009.
Office Action (Mail Date Aug. 23, 2011) for U.S. Appl. No. 12/440,792, filed Mar. 11, 2009.
Office Action (Mail Date Apr. 14, 2011) for U.S. Appl. No. 12/440,792, filed Mar. 11, 2009.

(Continued)

*Primary Examiner* — Sreeni Padmanabhan
*Assistant Examiner* — Svetlana M Ivanova
(74) *Attorney, Agent, or Firm* — Schmeiser, Olsen & Watts, LLP

(57) ABSTRACT

A docetaxel inclusion complex having improved water-solubility (up to 15 mg/ml) and stability (stability constant $Ka=2056M^{-1}-13051M^{-1}$), comprises docetaxel and hydroxypropyl-beta-cyclodextrin and/or sulfobutyl-beta-cyclodextrin in a ratio of 1:10-150. The method includes steps as follows: docetaxel dissolved in ethanol is added into water solution of cyclodextrin via stirring, until docetaxel is completely dissolved; said solution is filtered in 0.2-04 μm microporous membrane then ethanol is removed through reduced pressure to obtain the inclusion complex in a liquid form; or ethanol, followed by water is removed through reduced pressure, then dried to obtain the inclusion complex in a solid form.

9 Claims, 2 Drawing Sheets

OTHER PUBLICATIONS

Office Action (Mail Date Aug. 24, 2011) for U.S. Appl. No. 12/440,792, filed Mar. 11, 2009.

Office Action (Mail Date Jan. 25, 2012) for U.S. Appl. No. 12/440,792, filed Mar. 11, 2009.

Fossella, Frank V.; Single-Agent Docetaxel in Patients With Refractory Non-Small-Cell Lung; Dept. of Medical Oncology, The University of Texas M.D. Anderson Cancer Center, Oncology 11 (Suppl. 7):11-15, 1997.

Miller et al.; Phase II Trial of a 75-Mg/M2 Dose of Docetaxel With Prednisone Premedication for Patients With Advanced Non-Small Cell Lung Cancer; Thoracic Oncology Service, Division of Solid Tumor Oncology, Dept. Of Medicine, Cancer 1995, 75:968-72.

Grosse, P.Y.; In Vitro Modulation of Doxorubicin and Docetaxel Antitumoral Activity by Methyl-B-Cyclodextrin; European Journal of Cancer, vol. 34, No. 1, pp. 168-174, 1998.

Cao, Feng et al.; Progress in Hydrolysis of Carboxylic Esters Using Artificial Enzymes Cyclodextrins; Chinese Journal of Organic Chemistry, vol. 22, 2002, pp. 827-834.

Loftsson, Thorsteinn et al; Expert Opinion: Cyclodextrins in Drug Delivery; University of Iceland, 2005; pp. 335-351.

Medicine Forefront, Chinese Medicine Science and Technology Press, 2001: 17 pages.

Study on the Inclusion of Phenylpropanol/B2Cyclodextrin; Journal of China Pharmaceutical University, 2005, pp. 13-17.

Guidelines for Research Techniques of Chemicals Stimulation, Hypersensitivity and Hemolysis Tests, State Food and Drug Administration, Mar. 18, 2005, 31 pages.

Technical Requirements of Traditional Chinese Medicine Injection Study, State Food and Drug Adminstration, 1999, 5 pages.

Cao, Yuhua et al.; Study on Voltammetric Behavior of EU-VB6 and EU-VB6-GLY Complexes; China Academic Journal Electronic Publishing House; 2002, vol. 20, No. 6, 5 pages.

Xiaohua, Huang; Synthesis and Characterization of the Ternary Rare Earth Complex on Dysprosium-Glycine-Vitamineb; Journal of Suzhou Railway Teachers College, vol. 14, No. 4, Aug. 1997; 5 pages.

Cyclodextrin Chemistry, Science Press 2001, 3 pages.

* cited by examiner

PHARMACEUTICAL COMPOSITION CONTAINING DOCETAXEL-CYCLODEXTRIN INCLUSION COMPLEX AND ITS PREPARING PROCESS

FIELD OF THE INVENTION

The present invention relates to a pharmaceutical composition containing hydroxypropyl-sulfobutyl-β-cyclodextrin or sulfobutyl-β-cyclodextrin/docetaxel inclusion complex and the preparation method thereof.

BACKGROUND OF THE INVENTION

Docetaxel (trade name: Taxotere) is a synthesized compound after structural modification extracted from *Taxus baccata* leaves, a white or almost white crystalline powder, with molecular formula $C_{43}H_{53}NO_{14}$, chemical name: [2aR-(2aα, 4β,4aβ,6β,9α,(αR*,βS*),11α,12α,12aα,12bα)]-β-[[(1,1-dimethyl ethoxy)carbonyl]amino]-α-hydroxyphenyl propionic acid [12b-acetoxy-12-benzoyloxy-2a,3,4,4a,5,6,9,10,11,12,12a,12b-dodecahydro-4,6,11trihydroxyl-4a,8,13,13-tetramethyl-5-oxo-7,11-methylene-1H-pentacyclo-ene[3,4]benzo[1,2-b]tetraoxacyclo-9-base]acetate trihydrate. Its molecular weight is 807.19. This product is a new taxus anti-tumor drug, belongs to a fat-soluble compound, difficult to dissolve in water (2.903 μg/ml). Because the benzoyl group of the paclitaxel is substituted by t-butoxycarbonyl, the water-solubility of Docetaxel is slightly larger than that of Paclitaxel (0.25 μg/ml~0.60 μg/ml).

The anti-tumor mechanism of this product is the same as that of paclitaxel, which exerts its anti-tumor activity by inhibiting tubulin depolymerization. However, its inhibitory activity of tubulin depolymerization is about 2 times of that of paclitaxel, so it has a better curative effect on advanced breast carcinoma, superior to other single drug therapy (25%-53%) and stronger than antliracyclines, with an effective ratio of 49% for treatment of advanced breast carcinoma and better curative effects on advanced non-a-cell lung cancer, advanced ovarian cancer, pancreatic cancer, head and neck cancer and gastric cancer.

Docetaxel is insoluble in water and other commonly used medicinal organic solvent. It is used as injection in clinical application, and its injection solution is prepared with docetaxel Tween solution (injection specification: 1 ml, 20 mg/ml) and 13% ethanol and normal saline or glucose. The tween solution has a lower stability, stored at a low temperature of 2~8° C. in a dark place. The injection solution for clinical use is easily to precipitate. This product has similar side effects as paclitaxel, which may cause serious allergic reactions after injection, and the incidence rate of moderate and severe hypersusceptibility is as high as 25.9% (Oncology, 1997, 11 (7): 11); If the dosage is 75 mg/m² or 100 mg/m², the incidence rate of moderate hypersusceptibility or more is respectively 31% and 41.3% and the injection-part reaction rate can also be up to 13.3% (Cancer, 1995, 754: 968). Therefore, when docetaxel is used, allergic reaction prevention treatment should be conducted by taking large doses of hormones from PM 8:00 on the first day before the docetaxel treatment, generally taking dexamethasone 4.5 mg orally, once in the morning and once at night every day, for 3~5 days in succession; 30 min-60 min before injection of docetaxel, intramuscular injection of 40 mg diphenhydramine and 300 mg cimetidine were conducted to prevent from hypersensitivity. To prevent gastrointestinal reaction, intravenous injection of ondansetron or Nasea shall be conventionally conducted 30 min prior to chemotherapy. In addition, it is quite troublesome for clinical use of docetaxel, closely observing whether there are leaks or not in the process of fluid infusion; if any, the injection part must be immediately replaced and local blocking should be conducted with Hirudoid ointment for external use (3 times per day, for a few days). In addition, the conventional ECG monitoring should be carried out to closely observe the changes of breathing, heart rate and blood pressure, pay close attention to the occurrence of allergic reactions and make sure a good preparation of care rescue for severe allergic reactions. At present, improving the stability of docetaxel formulations and reducing the side effects become the focus of technical difficulties.

In recent years, researches on paclitaxel formulations mainly focus on liposomes, nano-granule, albumin cross-linked precursor, cyclodextrin inclusion and so on. The key technology focuses on biocompatibility, in vivo tolerance of the selected materials, paclitaxel solubilization and formulation stability, Similar to paclitaxel, for the docetaxel formulation improvement, the cyclodextrin inclusion technology is increasing widely used, and acet-γ-cyclodextrin, Hydroxypropyl-β-cyclodextrin and 2,6-dimethyl-β-cyclodextrin have been reported to use for docetaxel modification. Current study showed that application of cyclodextrin inclusion technology can not only enhance docetaxel stability, enhance its solubility, but also can significantly enhance the drug activity and reduce toxic and side effects. By using methyl-β-cyclodextrin/docetaxel inclusion and other drugs to determine their effects on the activity of a wide range of tumor cells $IC_{50}$ (European Journal of Cancer, 1998, 34: 168-174), it was discovered that, after adding methyl-β-cyclodextrin, docetaxel $IC_{50}$ CD was significantly reduced and $IC_{50}/IC_{50CD}$ values f different cells were within the scope ranging from 4.7-14.3, which proved that, cyclodextrin inclusion can significantly enhance the activity of docetaxel. The inclusion formulations made of acet-β-cyclodextrin or hydroxypropyl-β-cyclodextrin (WO9924073; CN1222321/ZL 98811010.5) can significantly reduce toxic and side effects of cardiovascular and respiratory system, but preferable technical solution in the invention is to prepare the composition with docetaxel/hydroxypropyl-β-cyclodextrin in a mass ratio of 1:133, the solubility of docetaxel is 0.75 mg/ml; if with the docetaxel/acetyl-γ-cyclodextrin in a mass ratio 1:50; the solubility of docetaxel can be up to 1.00 mg/ml, despite of increased docetaxel solubility, but each dose specification (20 mg) of docetaxel injection solution prepared by such technology still require not less than 1 ml ethanol as a cosolvent. If the existing technology is used to conduct cyclodextrin/docetaxel inclusion, which would be unable to meet the drug requirements for clinical use, the main problem is: The solubility of docetaxel after cyclodextrin inclusion is still relatively low, inconvenient for clinical use (need substantial solvent) and difficult to meet the suitable dosage requirements; application of substantial cyclodextrin will seriously affect practical applications; solubilization of inclusion with high doses of organic solvent can not only be conducive to cyclodextrin solubilization, but also increase the formulation irritation and reduce the patient's compliance. In aspect of technical methods, current technology only focuses on pharmaceutical stability of formulations (clarification/precipitation of the solution), while ignoring the drug chemical stability of especially for in the solution. Because cyclodextrin has the features of catalyzing ester compounds (Organic Chemistry, 2002; 22 (11):827-834), docetaxel containing ester-based side chains in solution could tend to stabilize due to cyclodextrin inclusion, or accelerate decomposition by cyclodextrin catalysis (cause decrease of stability). The inclusion is directly related to the stability and cyclodextrin structural property (type of cyclodextrin). These factors caused difficult extended application of current technology. Therefore, less use of cyclodextrin and no use or less use of organic solvents for improving the docetaxel solubility to meet the dose requirements of clinical application and maintaining the drug pharmaceutical nature and chemical stability are the technical problems for use of cyclodextrin inclusion technology in docetaxel.

At present, the cyclodextrin and cyclodextrin derivatives used to injection only include α-cyclodextrin, hydroxypropyl-β-cyclodextrin and sulfobutyl-β-cyclodextrin only (Expert Opin Drug Deliv, 2005 March; 2 (2): 335-51), among of which, hydroxypropyl-β-cyclodextrin is a neutral non-ionized derivative and sulfobutyl-β-cyclodextrin is an ionized derivative. Studies shows that (Medicine Forefront, Chinese Medicine Science and Technology Press, 2001: 46-59), sulfobutyl-β-cyclodextrin was significantly improved in safety, stability, drug solubilization and production preparation technology, etc. Recently, we researched and developed a new type of cyclodextrin derivative-hydroxypropyl-sulfobutyl-β-cyclodextrin (CN 1800221A), which has excellent performance and good safety. In the present invention, hydroxypropyl-sulfobutyl-β-cyclodextrin or sulfobutyl-β-cyclodextrin was used to improve docetaxel. The low proportion (mass ratio 1:17) of inclusion can promote the docetaxel solubility up to 15 mg/ml or higher. The prepared injection has a good pharmaceutical property and chemical stability, strong activity and low irritation. If the solid inclusion was diluted for 500 times, it can maintain stable for several days, with an important clinical application value.

SUMMARY OF THE INVENTION

The present invention is to overcome the drawbacks of low docetaxel solubility, poor pharmaceutical chemical stability; too high cyclodextrin ratio and much residual organic solvents, realize technological breakthroughs and provide a cyclodextrin docetaxel inclusion featuring in high docetaxel solubility and pharmaceutical stability, relatively low cyclodextrin content and small residual organic solvents so as to realize clinical application. The present invention also provides the preparation method of such inclusion composition.

For the present invention, the pharmaceutical composition containing cyclodextrin/docetaxel inclusion composes docetaxel, cyclodextrin and pharmaceutical acceptable excipient. Of which, the mass ratio of docetaxel and Cyclodextrin is 1:10~150; said cyclodextrin is hydroxypropyl-sulfobutyl-β-cyclodextrin or sulfobutyl-β-cyclodextrin or their mixture; the stability constant of the cyclodextrin/docetaxel inclusion is $Ka=2056M^{-1}\sim13051M^{-1}$.

Specifically, the said pharmaceutical composition comprising cyclodextrin/docetaxel inclusion is prepared as follow:

Docetaxel dissolved in ethanol is added into a water solution of hydroxypropyl-sulfobutyl-β-cyclodextrin or sulfobutyl-β-cyclodextrin or their mixture while stirring;

Until docetaxel is completely dissolved, the resulting solution is filtered in 0.2~0.4 μm microporous membrane;

Then ethanol is removed through reduced pressure to obtain the inclusion complex in a liquid form;

Or ethanol after water is removed through reduced pressure, then dried to obtain the inclusion complex in a solid form. The resulting inclusion contains small or trace amount of ethanol. Said "small or trace amount of ethanol" means that the content of ethanol in the solid inclusion is less than 2%.

In the present invention, hydroxypropyl-sulfobutyl-β-cyclodextrin or sulfobutyl-β-cyclodextrin aqueous solution was mixed with proper amount of docetaxel in ethanol. The ethanol can promote the inclusion. After inclusion is formed, the ethanol is removed to prepare a stable docetaxel/cyclodextrin inclusion. The composition of the inclusion and common pharmaceutical excipients was prepared into a pharmaceutical inclusion composition for clinical use, thus improving the docetaxel solubility, enhancing stability and reducing the side effects, to obtain docetaxel products for clinical applications. Preparation of inclusion is the key technology of the present invention.

The sulfobutyl-β-cyclodextrin used in the present invention is ionized cyclodextrin derivative and the pharmaceutical sulfobutyl-β-cyclodextrin is a derivative (product) of 6~7 substitutions ($SBE_7$-β-CD trade name: Captisol); and our developed hydroxypropyl-sulfobutyl-β-cyclodextrin (HP-SBE-β-CD) is a new type of cyclodextrin derivative (CN 1800221A) after substituted by hydroxypropyl and sulfobutyl combination, and this product has low toxicity, excellent performance inclusion superior to sulfobutyl-β-cyclodextrin, more suitable for non-oral preparations.

Under the present invention, the preparation method of pharmaceutical composition containing cyclodextrin/docetaxel inclusion is as follows:

Docetaxel is prepared into a solution with less ethanol as possible. Docetaxel dissolved in ethanol is added into a pure water solution of hydroxypropyl-sulfobutyl-β-cyclodextrin or sulfobutyl-β-cyclodextrin or their mixture while stirring;

Until docetaxel is completely dissolved, the resulting solution is filtered in 0.2~0.4 μm microporous membrane;

The ethanol is removed through reduced pressure giving a liquid inclusion, or ethanol after water is removed through reduced pressure, then dried to obtain the docetaxel inclusion complex in a solid form with the ethanol content of less than 2%.

More preferably and specifically, the detailed steps for preparation of pharmaceutical composition containing cyclodextrin/docetaxel inclusion are as follows:

The docetaxel and cyclodextrin in a weight ratio of 1:17 were used to prepare pure aqueous solution of cyclodextrin. The solution prepared with hydroxypropyl-sulfobutyl-β-cyclodextrin, or sulfobutyl-β-cyclodextrin, or their mixture and 2~10 times of pure water (in weight) was added with the mixed solution prepared by appropriate amount of docetaxel and ethanol (the ethanol amount depending on dissolution of docetaxel), while heating and stirring at room temperature or at a temperature of 25~65° C. After the inclusion formed, filtered through microporous membrane of 0.2~0.4 μm; then the ethanol was removed under reduced pressure to give a docetaxel solution containing small amount or trace amount of ethanol.

The water is removed from the aforesaid docetaxel solution through reduced pressure, and then dried under a vacuum condition through reduced pressure to obtain the solid docetaxel inclusion complex.

The resulting solid inclusion has a high water-solubility, easily dissolved without adding other cosolvents. The aqueous solution prepared has less side effect of hemolysis, suitable for clinical use. The solid inclusion containing 20 mg of docetaxel of clinical dosage was added with 10~1000 times of injection saline solution to prepare a solution, which could remain stable after a few days. And the other isotonic dose of pharmaceutical excipient added will basically not affect the stability of the solution.

The said solid inclusion and commonly-used injectable pharmaceutical excipient solution were diluted to appropriate concentration before subjecting to sterilization treatment. The resulting composition solution can be used for injection.

Validation of Inclusion Reaction:

Determination of system UV absorption is an effective way to identify inclusion (Cyclodextrin Chemistry, Science Press 2001, P135). The UV Spectroscopy test showed that, in aqueous solution, the UV absorption of docetaxel would vary with cyclodextrin concentration (no Cyclodextrin absorption itself) (FIG. 1). Docetaxel UV absorption would significantly enhance with the increase of cyclodextrin concentration, suggesting that docetaxel has a significantly strong inclusion with the cyclodextrin under the present invention.

Determination of Inclusion Stability Constant:

The inclusion stability constant Ka is used to determine the degree of inclusion and UV spectrophotometry is one of common methods to determine Ka. With the change of cyclodextrin concentrations, the UV absorption of docetaxel solution of constant concentration shows a regular change, and the relationship between cyclodextrin concentration (C) and UV absorbance (A) is obtained. From the relation curve of 1/C and 1/A, the Level-1 apparent stability constant Ka of cyclodextrin/docetaxel inclusion can be quantitatively calculated. Meanwhile, the changes of Ka after adding ethanol are determined in the test, and the Ka values of different cyclodextrins are shown in Table 1.

TABLE 1

The Level-1 apparent stability constant Ka of cyclodextrin/docetaxel inclusion($M^{-1}$; 231 nm)

| Cyclodextrin | Ka | |
|---|---|---|
| | $H_2O$ | 60% EtOH |
| Sulfobutyl-β-cyclodextrin | 2056 | 6968 |
| Hydroxypropyl-sulfobutyl-β-cyclodextrin | 13051 | 30117 |
| Hydroxypropyl-β-cyclodextrin | 582 | 2694 |
| β-cyclodextrin | 379 | |

The results showed that in docetaxel inclusion, the inclusion constant of β-cyclodextrin and hydroxypropyl-β-cyclodextrin is less than that of cyclodextrin used in the present invention, this may explain why the effects of prior arts are relatively poorer for the two cyclodextrins. Cyclodextrin used in the present invention has a larger inclusion constant Ka, and relevant test also showed that the presence of ethanol can significantly enhance the value of Ka and enhance the cyclodextrin inclusion ability, thus promoting the inclusion. The ethanol is not just used as a cosolvent in the inclusion process. Generally, when organic solvents compete with the drugs for inclusion, ethanol would reduce the Ka value of drugs (Journal of China Pharmaceutical University, 2005, 36 (1): 13-17). Unlike Hydroxypropyl-β-cyclodextrin, Cyclodextrin used in the present invention still had a higher Ka value after ethanol was removed in the pure water condition, enough to form a stable inclusion complex. Therefore, the ethanol was removed as far as possible to obtain a more pure drug inclusion and reduce the impact of ethanol on the drugs as far as possible. For the present invention, the impact of ethanol on the docetaxel inclusion is the technological basis for preparation of inclusion.

Preparation and Validation of Inclusion:

After adding appropriate amount of ethanol to make full inclusion, the ethanol was removed through reduced pressure, dried to prepare different proportions of docetaxel/cyclodextrin inclusion. DTA test confirmed that the solid substance is inclusion rater than simple physical mixture. Taking sulfobutyl-β-cyclodextrin/docetaxel (mass ratio of 1:17) as an example, it is analyzed and described as follows:

Four samples of docetaxel, sulfobutyl-β-cyclodextrin, physical mixture of docetaxel and sulfobutyl-β-cyclodextrin and inclusion were weighed, each for about 5.0 mg, to conduct differential scanning thermal analysis: reference: $Al_2O_3$, range: ±50 μV, temperature rise range: 30° C.~400° C., heating rate 10° C./min, and the DTA pattern was obtained. The results showed that: for docetaxel, a melting peak at 230° C. and endothermic decomposition at about 350° C.; for sulfobutyl-cyclodextrin, there is one dehydration endothermic peak and one phase transition peak at 70-90° C. and 250-270° C. respectively and melting endothermic decomposition at about 360° C. For the physical mixture, the endothermic peak characteristics of cyclodextrin and docetaxel maintained, while for the inclusion, the dehydration endothermic peak and phase transition peak basically disappeared and a new phase transition peak appeared at about 180° C. and exothermic decomposition at 360° C., and the position (temperature) and shape (thermal effect) of all peaks were significantly changed, therefore, it proved that the inclusion formed.

Residual Ethanol in Inclusion:

Inclusion $^1$HNMR showed a weak ethanol methyl peak. According to the integral area ratio of ethanol methyl peak (t, δ=1.10912) and cyclodextrin characteristic peak (H1 peak, d, δ=5.18257~5.05401), the residual ethanol amount (%) in inclusions prepared was calculated, the results were shown in Table 2,

TABLE 2

Residual ethanol level of docetaxel/cyclodextrin solid inclusion

| Inclusion batch No. | Cyclodextrin * | Drug/Cyclodextrin Ethanol | Residual volume (%) |
|---|---|---|---|
| 20060111 | a | 1:17 | 0.17 |
| 20060121 | b | 1:17 | 0.13 |
| 20060221 | a | 1:30 | 0.32 |
| 20060302 | b | 1:30 | 0.27 |
| 20060513 | b | 1:50 | 0.30 |
| 20060511 | a | 1:50 | 0.44 |
| 20060408 | a + b | 1:25:25 | 0.36 |
| 20060623 | b | 1:100 | 1.15 |

* a = Sulfobutyl-β-cyclodextrin; b = Hydroxypropyl-sulfobutyl-β-cyclodextrin

The test showed that, although more ethanol was used in the preparation process, there was less residual ethanol after purification. For the inclusion prepared with a low proportion of cyclodextrin (less than 1:50), generally the residual ethanol level was less than 1.0%; even for the inclusion prepared with a higher proportion of cyclodextrin, the residual ethanol level was less than 2.0%. Low residual ethanol level provided a favorable guarantee for improving the docetaxel stability and reducing irritation and other side effects.

Inclusion Solubilization Test:

Standard curve: 0.67 mg/ml docetaxel solution was prepared by dissolving docetaxel with ethanol, and diluted with pure water into 3.35 μg/ml~20.1 μg/ml series solutions, then UV absorption value A was measured under 228 nm. A standard curve was plotted by A against concentration C (mg/ml) (A=13.881C+0.3577 (r=0.9998)).

The excessive docetaxel or inclusion in the pure water was oscillated for 72 h at 25° C.±1° C., filtered and placed still. Appropriate amount of filtrate was fetched and diluted with pure water, then absorbance intensity values were measured at 228 nm to calculate the docetaxel solubility at 25° C. from the standard curve, the results were shown in Table 3.

TABLE 3

Docetaxel solubility in cyclodextrin solution

| Cyclodextrin * (drug proportion) | Solubility (mg/ml) | Solubilization Multiples |
|---|---|---|
| 0 | 0.002903 | 1 |
| a (1:17) | 15.007 | 5169 |
| b (1:17) | 15.547 | 5355 |

* a = Sulfobutyl-β-cyclodextrin; b = Hydroxypropyl-sulfobutyl-β-cyclodextrin

The results showed that cyclodextrin used in the present invention had a strong impact on docetaxel solubilization and the two cyclodextrins show insignificant difference on the docetaxel solubilization. Significant enhancement of docetaxel solubility was conducive to the preparation of stable non-oral preparations.

Sample Stability Test:

The pharmaceutical composition stability includes chemical stability of drug and pharmaceutical stability of composition.

Solid Inclusion Stability

HPLC chromatographic conditions: chromatographic column ODS $C_{18}$(250 mm×4.6 mm); mobile phase: water:acetonitrile (53:47); flow rate: 1.0 ml/min; detection wavelength: 230 nm; detection time: 30.00 min; detection sensitivity: 1.000AUFS.

Samples: docetaxel material; docetaxel/sulfobutyl-β-cyclodextrin inclusion (a, mass ratio of 1:17); docetaxel/hydroxypropyl-sulfobutyl-β-cyclodextrin inclusion (b, mass ratio of 1:17). Docetaxel materials and inclusions were divided into three portions of test samples equally and were subject to light, high temperature and high humidity acceleration tests respectively:

(1) Light Test

Samples were put in a sealed transparent container and then placed in an illumination box equipped with fluorescent light of 4500±500LX illumination intensity for 5 days. Sampling inspection analysis was conducted, and the test results were compared with the samples of 0 day.

(2) High Temperature Test

Samples were placed in a clean sealed container at a temperature of 60° C. for 5 days. Sampling inspection analysis was conducted, and the test results were compared with the samples of 0 day.

(3) High Humidity Test

Samples were placed in a sealed container of constant humidity at temperature of 25° C. and relative humidity of 90±5% for 5 days. Sampling inspection analysis was conducted, and the test results were compared with the samples of 0 day.

HPLC determination charts see FIG. 2 and FIG. 3. All test results see Table 4,

TABLE 4

Sample Content Determination of 5-day Acceleration Test

| | Content (%) | | | |
|---|---|---|---|---|
| Sample | 0 day | Light | High temperature | Hight humitdity |
| Docetaxel raw material | 99.675 | 90.176 | 87.859 | 83.877 |
| Inclusion a | 99.684 | 96.478 | 94.235 | 95.331 |
| Inclusion b | 99.645 | 97.985 | 95.407 | 95.310 |

Under the acceleration test conditions, docetaxel raw materials became slightly darker in color and the level decreased significantly; the inclusion appearance presented no color change, and the level decreased slightly and the impurities were basically unchanged. The results showed that, for the solid inclusion, the chemical property of docetaxel is stable and the inclusion technology had a significant effect on improving the stability of docetaxel.

Inclusion Solution and Pharmaceutical Stability (1) Solution Stability

A solid inclusion with mass ratio of 1:17 was dissolved into a liquid containing docetaxel of 15 mg/ml solution with normal saline or isotonic glucose solution, then diluted 1~1000-fold after sterilization treatment to prepare into different concentrations of injections observed for 5 h-10 d in succession. The observation results of docetaxel/hydroxypropyl-sulfobuty-β-cyclodextrin inclusion saline dilution system stability were shown in Table 5.

TABLE 5

State of cyclodextrin/docetaxel inclusion injection solution

| Dilution multiple | Drug concnetration mg/ml | Solution: State* | | | | | | | | |
|---|---|---|---|---|---|---|---|---|---|---|
| | | 0 h | 5 h | 10 h | 15 h | 20 h | 2 d | 4 d | 6 d | 10 d |
| 1 | 7.50 | + | + | + | + | + | − | − | − | − |
| 10 | 1.50 | + | + | + | + | + | + | + | + | + |
| 20 | 0.75 | + | + | + | + | + | + | + | + | + |
| 50 | 0.30 | + | + | + | + | + | + | + | + | + |
| 100 | 0.15 | + | + | + | + | + | + | + | + | + |
| 500 | 0.03 | + | + | + | + | + | + | + | + | + |
| 1000 | 0.015 | + | + | + | + | + | + | + | + | + |

*+: Clarification without precipitation; −: precipitation or turbidity (2) Docetaxel Stability Test in Solution (Assay)

Under the aforesaid HPLC chromatographic conditions, some docetaxel raw materials; docetaxel/sulfobuty-β-cyclodextrin inclusion (a) with a mass ratio of 1:17 and docetaxel/hydroxypropy-sulfobuty-β-cyclodextrin inclusion (b) with a mass ratio of 1:17 were taken and dissolved with normal saline solution, diluted for 100 times after 30 min ultrasonic wave treatment, placed still, and then the samples were taken to measure HPLC chromatogram at 0 h, 2 h, 4 h, 6 h, 8 h. Thus the docetaxel content in solution was obtained and the results were shown in Table 6.

TABLE 6

Changes of sample content in aqueous solution with time

| | Content (%) | | | | |
|---|---|---|---|---|---|
| Sample | 0 h | 5 h | 10 h | 24 h | 96 h |
| Docetaxel material | 99.675 | 99.025 | 97.381 | 93.433 | 86.384 |
| Inclusion a | 99.684 | 99.239 | 98.359 | 98.035 | 95.812 |
| Inclusion b | 99.645 | 99.554 | 99.002 | 97.459 | 96.386 |

Docetaxel was obviously decomposed, while the inclusion samples had stable chemical properties in aqueous solution and its content will remain basically unchanged within 10 hours. The half-life of sample decomposition in solution was as follows: 362.413 hours for docetaxel, 1341.035 hours for inclusion a and 1502.927 hours for inclusion b. The inclusion technology enhanced the docetaxel stability by 3.7 times and 4.15 times respectively.

Hemolysis Test:

(References: Guidelines for Research Techniques of Chemicals Stimulation, Hypersensitivity and Hemolysis Tests, State Food and Drug Administration, Mar. 18, 2005; Technical requirements of traditional Chinese medicine injection study", State Food and Drug Administration, 1999, 11, 12)

There is significant difference of the hemolysis between the inclusion saline solution and existing docetaxel formulations. The diluted solution of sulfobutyl-β-cyclodextrin inclusion (a) has a slight hemolysis, while the hydroxypropyl-sulfobutyl-β-cyclodextrin inclusion (b) has lower hemolysis, within the range of clinical administration concentration (about 0.08 mg/ml docetaxel content), there is basically no hemolysis, while the hemolysis of the existing docetaxel preparations is more than 20%. The results see FIG. 4.

ADVANTAGES OF THE INVENTION

The inclusion significantly improves the solubility of docetaxel (up to 15 mg/ml and above). After dilution, the solution can maintain clear and stable for a long time, with low hemolysis, less side effect and good pharmaceutical activity.

After inclusion of docetaxel and cyclodextrin, the solid and liquid samples have stable content, small proportion of drug/cyclodextrin, low dosage of cyclodextrin in the formulation, suitable for clinical use.

The inclusion in the present invention has less residual organic solvents, conducive to improve the medication safety.

The preparation method is simple, easy to operate, low cost without environmental pollution. The inclusion has stable property, good compatibility with other pharmaceutical excipients, suitable for preparation of formulations.

The injections prepared with inclusions contain no corrosive ingredients, no poisons, convenient for clinical use and high practicability.

DETAILED DESCRIPTION OF THE INVENTION

Example 1

Figure 1:
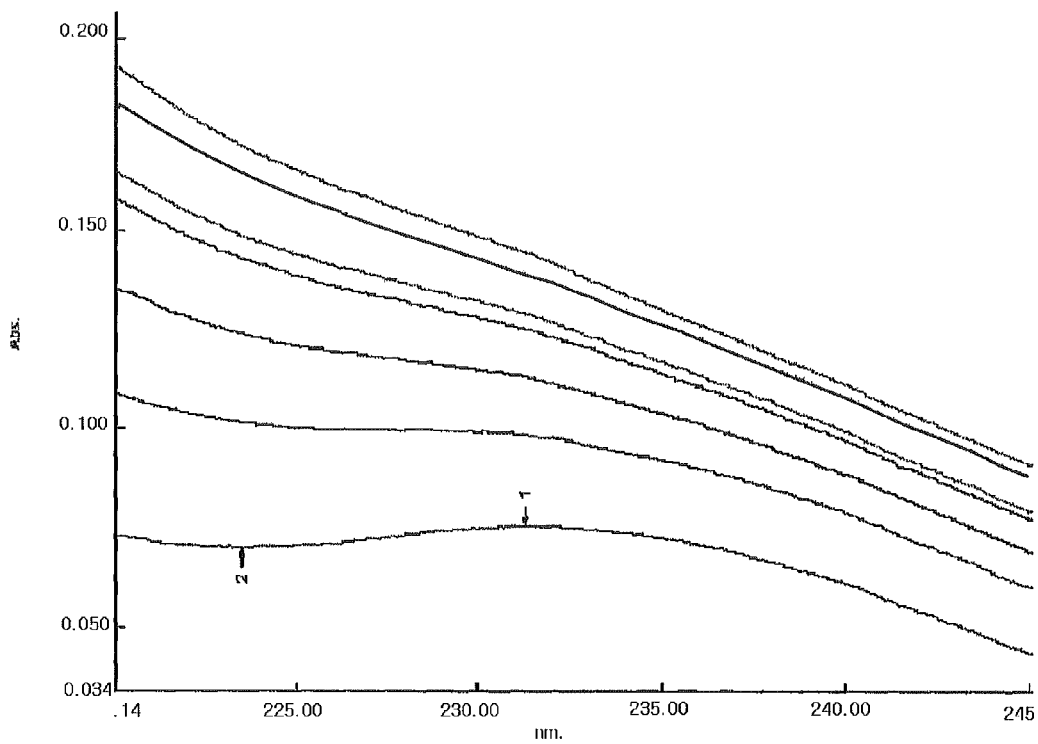
FIG. 1: Docetaxel UV absorption scanning (220 nm~245 nm) in aqueous solutions at different hydroxypropyl-β-cyclodextrin concentrations.
Figure 2:
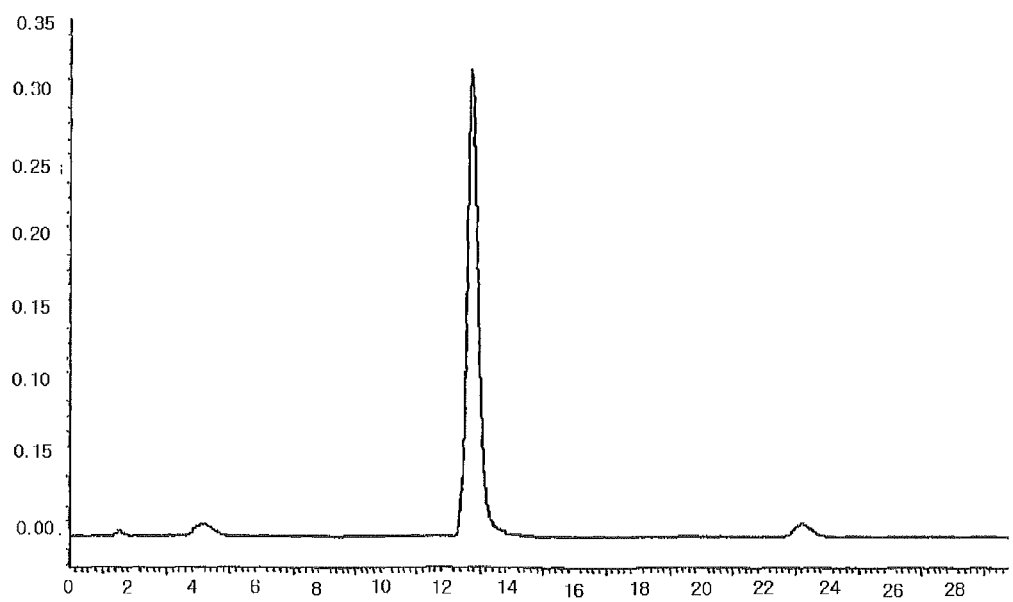
FIG. 2: HPLC chromatogram of docetaxel/hydroxypropyl-sulfobutyl-β-cyclodextrin inclusion high temperature test (5 d)
Figure 3:
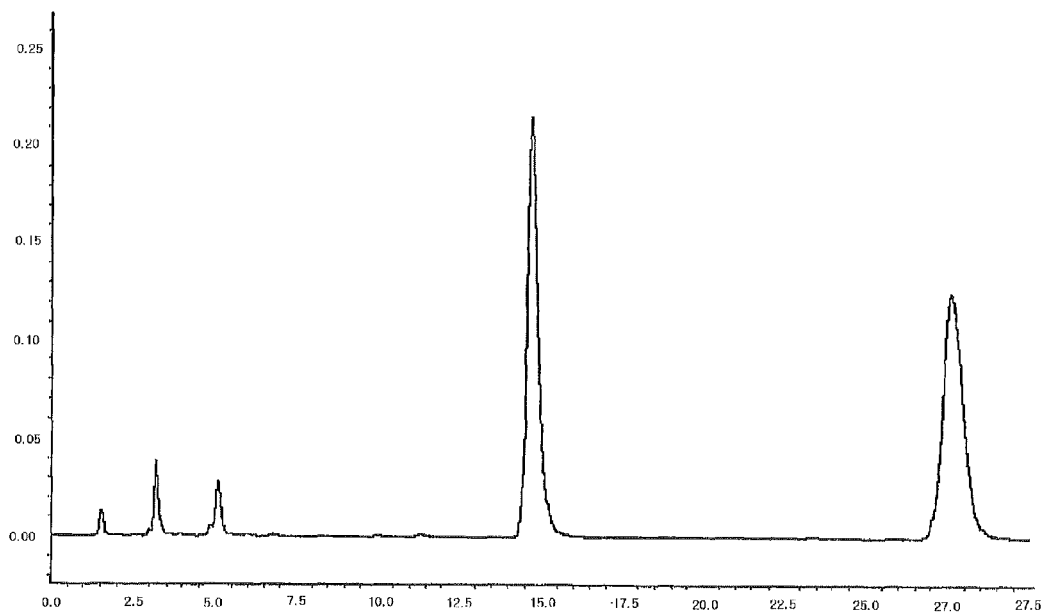
FIG. 3: HPLC chromatogram of docetaxel raw material high temperature test (5 d)
Figure 4:
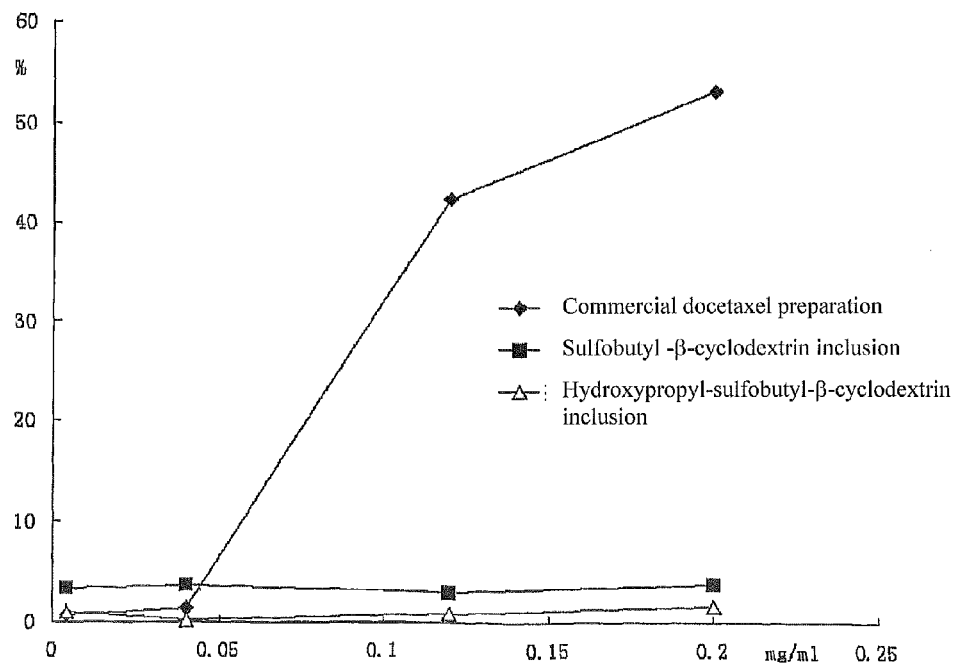
FIG. 4: Commercial docetaxel formulations, docetaxel/hydroxypropyl-sulfobutyl-β-cyclodextrin inclusion and docetaxel/sulfobutyl-β-cyclodextrin inclusion solutions diluted with normal saline solution and docetaxel concentration-hemolysis curve

1.70 g hydroxypropyl-sulfobutyl-β-cyclodextrin was mixed with 5.0 ml pure water, then added dropwise slowly with a solution prepared by 100.0 mg docetaxel and 1.0 ml ethanol while stirring. After fully mixed until complete dissolution, the resulting mixture was filtered through microporous membrane of 0.2~0.4 μm. The ethanol was removed from the filtrate at 55° C. under reduced pressure. After sterilization treatment, the water was also removed under reduced pressure until dried, and then the resulting solid product was dried for 48 h under reduced pressure giving a white solid inclusion.

The above powdered inclusion 360 mg (containing 20 mg docetaxel) was mixed and dissolved with 250 ml of normal saline injection to a liquid inclusion composition before used for injection.

Example 2 the procedure was carried out basically the same as example 1, but wherein 3.0 g hydroxypropyl-sulfobutyl-β-cyclodextrin was mixed with 15 ml pure water. The weight of docetaxel was 20 mg.

Example 3 the procedure was carried out basically the same as example 1, but wherein, the weight of docetaxel was 170 mg.

Example 4 the procedure was carried out basically the same as example 1, but wherein, the cyclodextrin was sulfobutyl-β-cyclodextrin.

Example 5 the procedure was carried out basically the same as example 2, but wherein, the cyclodextrin was sulfobutyl-β-cyclodextrin.

Example 6 the procedure was carried out basically the same as example 3, but wherein, the cyclodextrin was sulfobutyl-β-cyclodextrin.

Example 7 the procedure was carried out basically the same as example 1, but wherein, the cyclodextrin was the mixture of sulfobutyl-β-cyclodextrin and hydroxypropyl-sulfobutyl-β-cyclodextrin in a mass ratio of 1:1.

Example 8 the procedure was carried out basically the same as example 2, but wherein, the cyclodextrin was the mixture of sulfobutyl-β-cyclodextrin and hydroxypropyl-sulfobutyl-β-cyclodextrin in a mass ratio of 1:50.

Example 9 the procedure was carried out basically the same as example 3, but wherein, the cyclodextrin was the mixture of sulfobutyl-β-cyclodextrin and hydroxypropyl-sulfobutyl-β-cyclodextrin in a mass ratio of 50:1.

Example 10 the procedure was carried out basically the same as example 1, but, cyclodextrin and docetaxel were mixed with pure water firstly, added dropwise with ethanol slowly until the system was completely dissolved.

Example 11 the procedure was carried out basically the same as example 1, but, the resulting powdered inclusion was diluted with isotonic concentrations of glucose injection.

Example 12 the procedure was carried out basically the same as example 1, but, the resulting powdered inclusion was diluted with isotonic concentrations of fructose injection.

We claim:

1. A pharmaceutical composition comprising:
   a cyclodextrin/docetaxel inclusion which consists of docetaxel, cyclodextrin and a pharmaceutically acceptable excipient;
   wherein a mass ratio of docetaxel to cyclodextrin is 1:10~150;
   wherein the cyclodextrin is hydroxypropyl-sulfobutyl-β-cyclodextrin.

2. The pharmaceutical composition according to claim 1, wherein the docetaxel and cyclodextrin are in a mass ratio of 1:17~150.

3. A preparation method of the pharmaceutical composition comprising the cyclodextrin/docetaxel inclusion according to claim 1 is as follows:
   a solution of docetaxel in ethanol is added dropwise to an aqueous solution of hydroxypropyl-sulfobutyl-β-cyclodextrin while stirring.

4. The preparation method according to claim 3, wherein when the ethanol is removed under reduced pressure, the pressure reduction is continually maintained until the water is removed.

5. A pharmaceutical composition comprising:
   a cyclodextrin/docetaxel inclusion including docetaxel, cyclodextrin and a pharmaceutically acceptable excipient;
   wherein a mass ratio of docetaxel to cyclodextrin is 1:10~24;
   wherein the cyclodextrin is sulfobutyl-β-cyclodextrin; and
   wherein a stability constant of the cyclodextrin/docetaxel inclusion is $Ka=5396M^{-1}-14121M^{-1}$.

6. The pharmaceutical composition according to claim 5, wherein, a preparation method of the pharmaceutical composition comprises:
   adding a solution of docetaxel in ethanol dropwise to a pure water solution of sulfobutyl-β-cyclodextrin while stirring;
   filtering a resulting mixture through a microporous membrane of 0.2~0.4 µm after being dissolved; and
   removing the ethanol under reduced pressure, wherein a resulting product is dried under vacuum conditions, forming a liquid inclusion.

7. A preparation method of the pharmaceutical composition comprising the cyclodextrin/docetaxel inclusion according to claim 5 is as follows:
   adding a solution of docetaxel in ethanol dropwise to an aqueous solution of hydroxypropyl-sulfobutyl-β-cyclodextrin while stirring;
   filtering the resulting mixture through a microporous membrane of 0.2~0.4 µm after being dissolved; and
   removing the ethanol under reduced pressure to at least one of:
      give a liquid inclusion, and
      give a solid inclusion, wherein the water is also removed under reduced pressure and a resulting product is dried giving the solid inclusion;
   wherein the ethanol level of resulting inclusion is less than 1%.

8. The preparation method of claim 6 wherein the step of removing ethanol under reduced pressure further comprises:
   removing water under reduced pressure, wherein the resulting product is dried under vacuum conditions, forming a solid inclusion.

9. The preparation method according to claim 8 wherein an ethanol content of said solid inclusion is less than 1%.

* * * * *